United States Patent [19]

Heinsohn

[11] Patent Number: 4,694,101

[45] Date of Patent: Sep. 15, 1987

[54] PROCESS FOR SEPARATING METHYL ISOCYANATE

[75] Inventor: George E. Heinsohn, Elkton, Md.

[73] Assignee: E. I. Du Pont de Nemours and Company, Wilmington, Del.

[21] Appl. No.: 844,958

[22] Filed: Mar. 27, 1986

Related U.S. Application Data

[63] Continuation-in-part of Ser. No. 639,083, Aug. 9, 1984.

[51] Int. Cl.$^4$ ........................................... C07C 141/00
[52] U.S. Cl. .................................................. 560/352
[58] Field of Search ......................................... 560/352

[56] References Cited

U.S. PATENT DOCUMENTS 4,207,251  6/1980  Heyboer .............................. 560/352

FOREIGN PATENT DOCUMENTS 0218897  2/1985  Fed. Rep. of Germany ...... 560/352

Primary Examiner—Alan Siegel
Attorney, Agent, or Firm—Craig H. Evans

[57] ABSTRACT

Methyl isocyanate can be separated in high yields from a gas-phase mixture of the isocyanate and water by sequentially condensing a major portion of the water, adsorbing essentially all the remaining water from the mixture, and liquefying the methyl isocyanate.

6 Claims, No Drawings

PROCESS FOR SEPARATING METHYL ISOCYANATE

CROSS-REFERENCE TO RELATED APPLICATION

This application is a continuation-in-part of parent application U.S. Ser. No. 639,083 filed Aug. 9, 1984, now pending.

BACKGROUND OF THE INVENTION

U.S. Pat. No. 4,207,251 discloses the gas phase production of $C_1$-$C_{24}$ organo-isocyanates by oxidative dehydrogenation of the corresponding N-monosubstituted formamides. This process also forms one mole of water for every mole of isocyanate, however, and since these two products are reactive toward each other, their quick and efficient separation is essential to the recovery of the desired isocyanate in high yields. Although this patent discloses various methods of isolating the isocyanate from the hydrous gas phase, the methods are largely inefficient, or even inapplicable, with respect to methyl isocyanate in particular. Because methyl isocyanate is more reactive towards water, especially in the liquid phase, than are the other isocyanates, it is particularly important to separate them quickly and efficiently, without allowing their liquid phase contact, to ensure high recovery of the methyl isocyanate itself.

SUMMARY OF THE INVENTION

The present invention provides a process for separating methyl isocyanate from a gas-phase mixture containing methyl isocyanate and water vapor comprising, in order (a) diluting the gas-phase mixture by addition of an inert, relatively noncondensable gas such as nitrogen, such that the dew point of the methyl isocyanate in the mixture is lowered to about $-5°$ C. to $5°$ C.;

(b) removing a portion of the water vapor by cooling the mixture to a temperature which is about $5°$-$10°$ C. above the dew point of the methyl isocyanate in the mixture, to condense the water vapor;

(c) removing essentially all the remaining water vapor from the gas-phase mixture by passing the mixture over or through a water-absorbing material; and (d) liquefying the methyl isocyanate.

DETAILED DESCRIPTION OF THE INVENTION

The present invention relates primarily to the recovery and isolation of methyl isocyanate (MIC) from a gas-phase product stream resulting from a reaction in which water is co-produced. An example of such a reaction is described in U.S. Pat. No. 4,207,251. Although the invention will be described in this context, it will be evident that it has direct application to the recovery of MIC from any water-containing gas-phase mixtures.

In order to obtain high yields of MIC from any reaction in which water is co-produced, it is necessary to prevent any substantial further reaction between the two products. MIC and water react only very slowly in a vapor phase, but their reaction is greatly accelerated if they have contact in the liquid phase. The present invention takes advantage of the differences in boiling points between MIC and water to minimize this contact. For example, the reaction as described in U.S. Pat. No. 4,207,251 generates a gas-phase product mixture of water, MIC, unreacted monomethyl formamide (MMF) and several by-products. Of these, water, MMF, and the majority of by-products have boiling points higher than $80°$ C., and therefore these higher boiling components can be liquefied and removed from the gas stream without also liquefying the MIC, by controlled cooling with optional pressurization of the gas-phase reaction product mixture. After the first cooling stage, residual water vapor is removed from the remaining gas mixture by adsorption onto an appropriate material. Finally, MIC (normal boiling point $39°$ C.), still in gas-phase and possibly mixed with carbon dioxide as another reaction by-product, is recovered by subjecting the mixture to further cooling, with optional pressurization, to liquefy the MIC.

The first step of the process of the invention is to cool the mixture to a temperature sufficiently low to condense the water vapor but above the dew point of MIC in the mixture. As used herein, "MIC dew point" is the temperature at or below which MIC vapor condenses at a rate sufficient to form a separate liquid MIC phase. As those skilled in the art will recognize, the MIC dew point will vary, depending on the composition of the gas-phase mixture itself, but it can be readily calculated by available methods. This cooling step is conveniently carried out by passing the gas mixture through standard condensing equipment of the non-contact variety. Shell-and-tube type condensers are preferred.

A preferred mode of operation in the cooling step is to adjust the composition of the gas stream by the addition of an inert, relatively noncondensable gas, such as nitrogen, to lower the dew point of the MIC. By this procedure, the mixture can be cooled to temperatures which are sufficiently low to condense the water rapidly and to depress its vapor pressure, thereby keeping the amount of residual water vapor in the gas stream small, but which are still above the depressed MIC dew point. In this manner, no MIC is lost in the cooling step other than a small fraction that may dissolve in the condensing water. In general, it is preferred to cool the gas mixture to a temperature that is about 5–10 degrees above the MIC dew point. In this context, good results are obtained when the MIC dew point is lowered so that the gas mixture can be cooled to about $0°$-$10°$ C., (MIC dew point lowered to $-5°$ C. to $5°$ C.) with operation at about $0°$-$5°$ (MIC dew point lowered to $-5°$ C. to $0°$ C.) being preferred.

The second step of the process of this invention is to remove the residual water vapor from the gas mixture through adsorption of the vapor. This step is performed by passing the gas mixture, preferably immediately upon completion of the initial cooling step, over or through a water-adsorbing material. Suitable materials are those which have an affinity for the water vapor and which are not reactive with methyl isocyanate. Molecular sieves of the 3A, 5A, or 13X designation, for example, are suitable, with those of the 3A type preferred.

Under normal adsorption operation according to methods known in the art, particularly with molecular sieves as described above, essentially all water will be removed. That is, the resultant gas mixture will be sufficiently free of water vapor that no appreciable loss of MIC will occur in the final liquefaction step from reaction with co-condensed residual water vapor. With use of a 3A molecular sieve, for example, water vapor levels as low as 50 parts per million or less in the gas mixture are readily achievable. Time of contact with the molecular sieves is not critical, and a residence time of 2 seconds has provided proper drying. It is expected that lower residence times will give desired results as well. Higher residence times can be used, although for reasons of economic efficiency and practicality in choice of equipment, times above 30 seconds are not necessary.

Operating conditions of the adsorption step are not critical, although the adsorbing material must be periodically replaced or regenerated to avoid loss of MIC from reaction of MIC vapor with built-up adsorbed water. Molecular sieves, for example, can be regenerated by heating to about 200°-400° C. under a flow of nitrogen for 20-30 minutes. A suitable nitrogen flow rate is one that causes a volume equal to 4 times the volume of the sieves to pass through the sieves each minute.

The final step of liquefying the MIC to separate it from the gas stream can be effected by cooling, pressurization, or a combination of these. At this step, depending on the source of the gas mixture, in addition to MIC the gas mixture may include normal air, carbon dioxide, nitrogen, or a combination of these and other relatively noncondensable gases. The procedure used to liquefy the MIC will depend, in part, on the relative volume of these other gases.

The optimum temperature and pressure for liquefaction will also depend on the dew point of MIC in the final gas mixture, and it will be recognized that greater levels of nitrogen in the gas mixture, for example, will lower the MIC dew point. Although any temperatures below the MIC dew point will be effective, generally temperatures of from about −65° C. to +10° C., depending on the MIC concentration and the corresponding use of pressure, as described below, provide recovery of up to 95% of the MIC in the final gas stream. The liquefaction step can be performed at atmospheric pressure (100 kPa), but pressurization of the gas-phase mixture will further aid in liquefying the methyl isocyanate, and any pressure can be used. However, for reasons of practicality, in choice of equipment and in terms of additional yield provided, pressurization to greater than 100 psig (690 kPa) is not necessary. Preferably, pressures of 35-50 psig (240-345 kPa) are used. The MIC liquefaction can be effected by passing the gas mixture through standard condensing equipment such as the non contact shell-and-tube variety.

EXAMPLES 1-3

A gas-phase mixture of 27 mole % water, 18 mole % MIC, 54 mole % nitrogen, and 1 mole % monomethyl formamide was passed at approximately atmospheric pressure at a flow rate of 4.44 liters per minute through a first vertically-mounted, straight-bore laboratory condenser (30.5 cm in length, 1.9 cm inside diameter) packed with 0.32 cm diameter glass beads and jacketed with chilled water to provide temperature control. The temperature to which the gas-phase mixture was cooled in each example is shown in the table below. The gas-phase mixture exiting the condenser was passed through a glass tube (28 cm in length, 24 mm inside diameter) containing 60 grams of type 3A molecular sieves, and then was passed through a second condenser, where the MIC was liquefied and collected. The second condenser was of the same construction and dimension as the first condenser but was filled with stainless steel packing and jacketed with refrigerated methanol to cool the mixture to a temperature of −62° C. to −60°C. (atmospheric pressure). This temperature and pressure were used in all three examples.

The results of Examples 1-3 are summarized in the following Table I. In the Table, the quantities of MIC removed in the first condenser, in the sieves, and ultimately recovered in the second condenser are expressed as weight percentages of the original amount of MIC in the feed gas mixture.

TABLE I

| Example | First Condenser Temperature | MIC in First Condenser | MIC in Sieves | MIC Recovered Second Condenser |
| --- | --- | --- | --- | --- |
| 1 | 4-6° C. | 1% | 3% | 85% |
| 2 | 12-15° C. | 4% | 4% | 80% |
| 3 | 23-28° C. | 3% | 6% | 74% |

EXAMPLE 4

Liquid monomethyl formamide (1.6 g/min.), air 1575 (cc/min.), and nitrogen (375 cc/min.) were passed into an electrically heated vessel held at 210° C. at atmospheric pressure, and the resulting heated vapors were then passed through a U-tube (1.27 cm outside diameter) maintained at 450° C. and containing 8 grams of silver crystals arranged in a bed 2.54 cm thick. The gas-phase mixture exiting the U-tube was passed through a first vertically-mounted, straight-bore condenser (30.5 cm in length, 0.95 cm outside diameter) packed with 4 mm diameter glass beads and jacketed with chilled water to provide temperature control. The gas-phase mixture exited the condenser at a temperature of about 5°-7° C. and was then passed through a metal tube (2.54 cm outside diameter, 46 cm in length) containing 181 grams of 3A molecular sieves, and then was passed through a second condenser where the MIC was liquefied and collected. The second condenser was a vertically-mounted, straight-bore condenser (0.64 cm outside diameter, 36 cm in length) jacketed with a refrigerated mixture of ethylene glycol and water to cool the gas-phase mixture to a temperature of −29° C. to −26° C. The second condenser was operated at a pressure of 35 psig (240 kPa). During the test period 904 grams of monomethyl formamide were fed into the system, and 611 grams of MIC were isolated from the second condenser.

What is claimed is:

1. A process for separating methyl isocyanate from a gas-phase mixture containing methyl isocyanate and water vapor comprising, in order
   (a) diluting the gas-phase mixture by addition of an inert, noncondensable gas, such that the dew point of the methyl isocyanate in the mixture is lowered to about −5° C. to 5° C.;
   (b) removing a portion of the water vapor by cooling the mixture to a temperature which is about 5°-10° C. above the dew point of the methyl isocyanate in the mixture, to condense the water vapor;
   (c) removing essentially all the remaining water vapor from the gas-phase mixture by passing the mixture over or through a water-absorbing material; and
   (d) liquefying the methyl isocyanate.

2. A process according to claim 1, wherein the water-absorbing material is a molecular sieve.

3. A process according to claim 2, wherein said inert gas is nitrogen.

4. A process according to claim 3, wherein sufficient nitrogen is added to the gas-phase mixture to lower the dew point of the methyl isocyanate in the mixture to −5° C. to 0° C.

5. A process according to claim 4, wherein liquefying step (c) includes cooling the gas-phase mixture to a temperature of between −65° C. and 10° C.

6. A process according to claim 5, wherein liquefying step (c) includes pressurizing the gas-phase mixture to a pressure no higher than 690 kPa.

* * * * *